United States Patent [19]
Monroe

[11] Patent Number: 5,356,368
[45] Date of Patent: * Oct. 18, 1994

[54] METHOD OF AND APPARATUS FOR INDUCING DESIRED STATES OF CONSCIOUSNESS

[75] Inventor: Robert A. Monroe, Nelson County, Va.

[73] Assignee: Interstate Industries Inc., Faber, Va.

[ * ] Notice: The portion of the term of this patent subsequent to May 25, 2010 has been disclaimed.

[21] Appl. No.: 664,176

[22] Filed: Mar. 1, 1991

[51] Int. Cl.$^5$ ............................................. A61M 21/00
[52] U.S. Cl. ...................................... 600/28; 128/732
[58] Field of Search ................................... 600/26–28; 128/731–732

[56] References Cited

U.S. PATENT DOCUMENTS

| | | |
|---|---|---|
| 2,466,054 | 4/1949 | Siebel . |
| 3,160,159 | 12/1964 | Hoody et al. . |
| 3,576,185 | 4/1971 | Schulz et al. . |
| 3,712,292 | 1/1973 | Zentmeyer, Jr. . |
| 3,753,433 | 8/1973 | Bakerich et al. . |
| 3,826,243 | 7/1974 | Anderson . |
| 3,837,331 | 9/1974 | Ross . |
| 3,884,218 | 5/1975 | Monroe . |
| 4,034,741 | 7/1977 | Adams et al. . |
| 4,141,344 | 2/1979 | Barbara . |
| 4,227,516 | 10/1980 | Meland et al. . |
| 4,335,710 | 6/1982 | Williamson . |
| 4,573,449 | 3/1986 | Warnke . |
| 4,834,701 | 5/1989 | Masaki . |
| 4,883,067 | 11/1989 | Knispel et al. ........................ 600/28 |
| 5,036,858 | 8/1991 | Carter et al. . |
| 5,101,831 | 4/1992 | Koyama et al. ........................ 600/26 |

Primary Examiner—Lee S. Cohen
Assistant Examiner—J. P. Lacyk
Attorney, Agent, or Firm—Sughrue, Mion, Zinn, Macpeak & Seas

[57] ABSTRACT

Improved methods and apparatus for entraining human brain patterns, employing frequency following response (FFR) techniques, facilitate attainment of desired states of consciousness. In one embodiment, a plurality of electroencephalogram (EEG) waveforms, characteristic of a given state of consciousness, are combined to yield an EEG waveform to which subjects may be susceptible more readily. In another embodiment, sleep patterns are reproduced based on observed brain patterns during portions of a sleep cycle; entrainment principles are applied to induce sleep. In yet another embodiment, entrainment principles are applied in the work environment, to induce and maintain a desired level of consciousness. A portable device also is described.

28 Claims, 21 Drawing Sheets

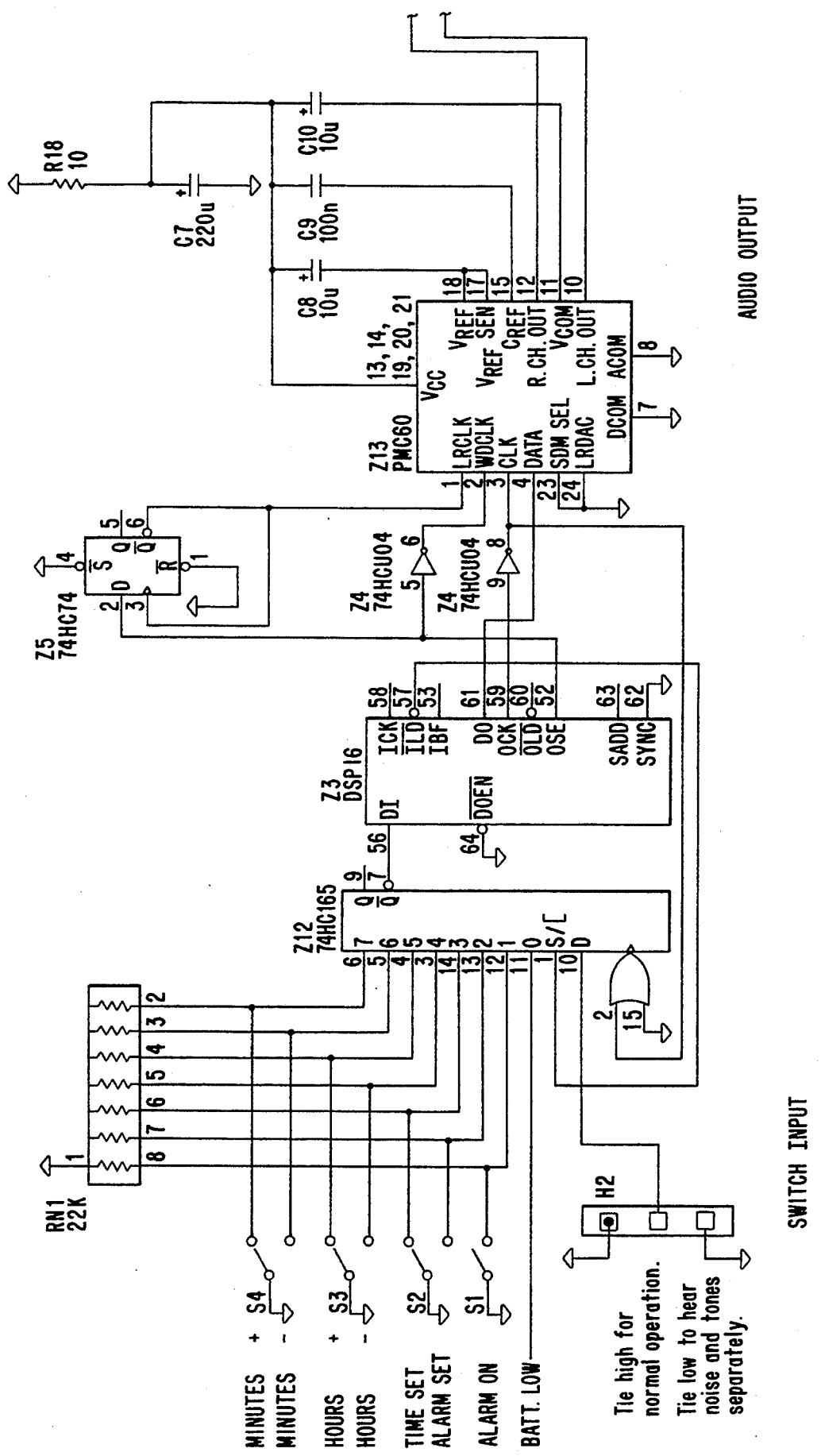

"Baseline" Brain Waves
AMPLITUDE (uV)

POWER (%uV$^2$pp)
0-4Hz= 18.8%
4-8Hz= 9.2%
8-12Hz= 16.2%
12-30Hz= 49.2%

FIG. 9B

MOOD-MINDER Stimulus Frequencies
POWER ($uV^2pp$)

[Graph showing peaks near 16 Hz and 21 Hz, x-axis 0–60 Hz, y-axis 0–10]

POWER(%$uV^2pp$)

16 Hz = 47.6%
21 Hz = 23.2%

Awake and Alert

FIG. 9C

MOOD-MINDER Stimulus Wave
AMPLITUDE (uV)

[Waveform, y-axis -30 to 30 uV]

POWER(%$uV^2pp$)

16 Hz = 47.6%
21 Hz = 23.2%

Awake and Alert

FIG. 9D

MOOD-MINDER Response Brain Wave
AMPLITUDE (uV)

[Waveform, y-axis -30 to 30 uV]

POWER(%$uV^2pp$)

16 Hz = 46.5%
21 Hz = 23.7%

Awake and Alert

POWER(‰uV²pp)
21Hz= 13.3%
8Hz= 22.1%
4Hz= 35.5%

Concentration

POWER(‰uV²pp)
21Hz= 13.3%
8Hz= 22.1%
4Hz= 35.5%

Concentration

POWER(‰uV²pp)
21Hz= 14.3%
8Hz= 21.5%
4Hz= 31.5%

Concentration

POWER(‰uV²pp)

16Hz= 11.5%
7Hz= 28.4%
4Hz= 30.2%

Attention

POWER(‰uV²pp)

16Hz= 11.5%
7Hz= 28.4%
4Hz= 30.2%

Attention

POWER(‰uV²pp)

16Hz= 8.2%
7Hz= 28.7%
4Hz= 32.6%

Attention

MOOD-MINDER Stimulus Frequencies
POWER ($uV^2pp$)

POWER($\%uV^2pp$)

6Hz= 9.5%
4Hz= 15.4%
1.5Hz= 19.6%

Relaxation

MOOD-MINDER Stimulus Wave
AMPLITUDE (uV)

POWER($\%uV^2pp$)

6Hz= 9.5%
4Hz= 15.4%
1.5Hz= 19.6%

Relaxation

MOOD-MINDER Response Brain Wave
AMPLITUDE (uV)

POWER($\%uV^2pp$)

6Hz= 7.9%
4Hz= 16.8%
1.5Hz= 20.0%

Relaxation

METHOD OF AND APPARATUS FOR INDUCING DESIRED STATES OF CONSCIOUSNESS

CROSS-REFERENCE TO RELATED APPLICATION

The present application is related to copending application No. 07/514,460, filed Apr. 16, 1990 now U.S. Pat. No. 5,213,562.

BACKGROUND OF THE INVENTION

1. Field of the Invention

The present invention relates to an improved method of inducing desired states of consciousness, including different levels of sleep, in human beings, using a technique known as frequency following response (FFR), developed by the present inventor. The invention also relates to apparatus for performing the method. A number of areas of applicability of the invention are described, in accordance with different preferred embodiments.

2. Description of the Background Art

In a prior patent, U.S. Pat. No. 3,884,218, the present inventor described a method of inducing different levels of sleep, using the FFR technique, in which brain waves could be made to follow superimposed frequency patterns. These frequency patterns were provided as sine waves, at frequencies known to correspond to different levels of sleep, such as alpha (exhibiting brain wave activity in the range of 8–12 Hz), theta (6–8 Hz), and delta (1–4 Hz). EEGs exhibiting frequencies between 12 and 30 Hz (known as a beta range) are characteristic of awake individuals, though beta activity at even higher frequencies has been observed in different types of mental activities. Gamma activity has been characterized as all activity above 30 Hz; until recently, it has not been possible to monitor brain activity in the gamma range. (It should be noted that the boundaries between gamma and beta, beta and alpha, alpha and theta, and theta and delta are somewhat arbitrary; the foregoing delineations are intended to be exemplary and not limiting.)

The present inventor discovered that the human brain could be entrained to output brain wave patterns these different frequencies. While frequencies corresponding to these different levels of sleep are not audible, by superimposing those frequencies on some type of sound, such as music, it was determined to be possible to induce desired levels of sleep. The individual listening to the music would "hear" the low frequencies, with the desired effect on brain activity.

An improvement on the inventor's patented technique, to induce varied states of alertness, is the subject of copending Application No. 07/514,460, the contents of which are hereby incorporated herein by reference. This copending application describes a general FFR technique using what is known as a binaural beat phenomenon, details of which are provided in that application. Briefly, a binaural beat is produced by sending signals at different frequencies (some Hz apart, depending on the desired effect) to an individual's left and right ears. The difference between the frequencies defines the frequency of the binaural beat. Using this technique, the desired frequency can be introduced into the individual's brain activity, inducing the desired state of consciousness.

The induction of FFR in the human brain in this manner results in the synchronization of activity in the hemispheres of the brain. FIG. 1A shows brain activity without FFR, and FIG. 1B shows brain activity with FFR. The inventor has coined the term HEMI-SYNC (for Hemisphere Synchronization) to describe this phenomenon.

The copending application describes a technique wherein, in one form, sine waves having a frequency corresponding to a consciousness state are superimposed on two different carrier frequencies to form two different signals to set up the binaural beat. In another form, an actual brain pattern, based on an electroencephalogram (EEG) waveform indicative of that consciousness state is superimposed on the different carrier frequencies to form two different signals. In use, each signal is provided to one ear of a subject. The difference in carrier frequencies sets up the binaural beat.

Another, more limited application of the binaural beat phenomenon is found in U.S. Pat. No. 4,834,701. In contrast to the narrow range of frequencies discussed in that patent, in the above-mentioned copending application, the applicability of the binaural beat phenomenon is investigated over a much wider range of frequencies, spanning the spectrum of brain activity.

Through additional investigation involving mapping of brain activities of different individuals, the present inventor has discovered some significance to the fact that, while brain waves at certain frequencies are characteristic of different levels of sleep, brain patterns of different individuals still vary. The inventor has investigated possible enhancements to the FFR effect by making it more generic among individuals, yet still more specific to brain activity than a simple sine wave, or an EEG of a particular individual.

Another area of investigation being performed by the present inventor relates to human sleep patterns. Based on current knowledge of human sleep patterns, it appears that sleep is composed of a series of 90-minute cycles. As stated earlier, the beta stage is one of alertness. The first sleep state is alpha, or mental and physical relaxation. The second is theta, or light sleep. Next is delta, or deep sleep. The inventor has investigated the possibility of providing FFR waveforms in cyclic patterns, replicating these human sleep patterns, to facilitate sleep. Another possibility is to take advantage of the cyclic nature of sleep patterns to provide a more gentle wake-up for a sleeper.

In considering the need for alertness during activities such as work, the inventor also considered how it might be possible to introduce FFR waveforms into ambient noise in one's surroundings to facilitate maintenance of desired states of consciousness. Particularly in environments such as factories, or in offices where office equipment puts out consistent types of noise, it would be desirable to be able to introduce a binaural beat into that noise at different frequencies, to enhance the degree of alertness of factory or office workers as desired.

SUMMARY OF THE INVENTION

In view of the foregoing, according to one aspect of the invention, EEGs for a number of individuals in different states of consciousness are sampled, and EEG waveforms for the group of individuals, corresponding to each identifiable state of consciousness, are combined. A binaural beat then is generated using the combined EEGs.

According to this aspect of the invention, it has been determined that using groups of EEG waveforms from different individuals and combining them to obtain a representative waveform yields a waveform that a person's brain is more likely to replicate than an individual EEG waveform, or a sine wave representation of the EEG waveform. The combination may be simple averaging, though other combination techniques, such as weighted averaging, for combining different numbers of EEG waveforms as desired, are contemplated. Now that the inventor has discovered that combinations of EEG waveforms provide a particularly effective entrainment environment, it will be seen that various ways of combining these waveforms may yield greater or lesser effects.

In accordance with another aspect of the invention, a method for replicating cyclic sleep patterns for a desired sleep period is provided. In a preferred embodiment according to this aspect of the invention, a subject is led from beta, to alpha, to theta, to delta, then back to theta, then alpha, then a rapid-eye movement (REM) or light dreaming sleep, in a sequence of 90-minute cycles, during a sleep period of desired duration. After the expiration of the period, the subject may wake up voluntarily. Alternatively, the invention can provide a gentle external stimulus to lead the subject to a beta state.

With respect to this aspect of the invention, an apparatus is provided which automatically leads an individual through these cyclic sleep patterns, and enables the individual to set a desired sleep period. This device preferably takes advantage of the techniques to be described relative to the first-mentioned aspect of the invention, but is not so limited. The inventive contributions of this second aspect of the invention are considered to lie in the combination of hardware itself which generates the desired sequence of binaural beats, as opposed to the particular software which determines the nature of those binaural beats. In one form, the invention is constituted by an alarm clock which provides a fade-in theta-alpha signal followed by a strong beta-gamma signal shortly before a desired wake-up time.

According to yet another embodiment of the invention, selectable mind-affecting sound patterns are provided to supplement constant ambient noise in any environment. When the noise is not present, the patterns are not provided. The patterns vary in amplitude in accordance with changes in the environmental noise.

In accordance with still another embodiment of the invention, a portable system is provided to enable the wearer to introduce binaural beat signals of frequencies that are selectable in accordance with a desired level of awareness. Depending on the level of sophistication of the device, the binaural beat may be generated using the combined EEG waveforms of the first aspect of the invention, but this last aspect of the invention is not so limited.

BRIEF DESCRIPTION OF THE DRAWINGS

The foregoing and other aspects of the invention will be understood by those of working skill in this technological field by reference to the following detailed description of the preferred embodiments of the invention, read in conjunction with the accompanying drawings, wherein:

FIGS. 9A–9M are graphs of different possible effects of the embodiment of FIGS. 8A and 8B, showing a baseline brain pattern, selected stimulus frequencies and corresponding stimulus waves, and associated response waves.

DETAILED DESCRIPTION OF THE PREFERRED EMBODIMENTS

The method according to a first preferred embodiment of the invention, which has been developed through extensive experimentation, derives from the empirically-observed phenomenon that brain patterns of human subjects are entrained more readily to brain patterns which more closely match their own. In prior implementations of the FFR technique, such as in the inventor's prior patent, in which sine waves having frequencies corresponding to desired levels of sleep were superimposed upon a given frequency, entrainment did occur. Use of the binaural beat phenomenon yielded better results, through synchronization of the hemispheres of the brain.

However, simple repetitive frequencies, or even combinations of such frequencies within different ranges, do not represent brain patterns per se, but rather provide entrainment environments for the brain to follow. It has been determined that, the more closely the entrainment environment parallels normal brain function at different levels of consciousness, the more effective the entrainment effect. This phenomenon is what led to the improvement disclosed in the above-mentioned copending application.

As a further improvement on that technique, as mentioned above, the present inventor investigated the possibility of creating more generic models of brain function at different levels of consciousness. As a result of that investigation, it was determined that combinations of EEG waveforms from different individuals functioning at the same identifiable level of consciousness (e.g. alpha sleep, theta sleep, or delta sleep) provided a superior entrainment environment. In the inventive method according to this aspect of the invention, the brain patterns of 40 to 50 individuals were combined to yield the entrainment environment.

Figure 3:
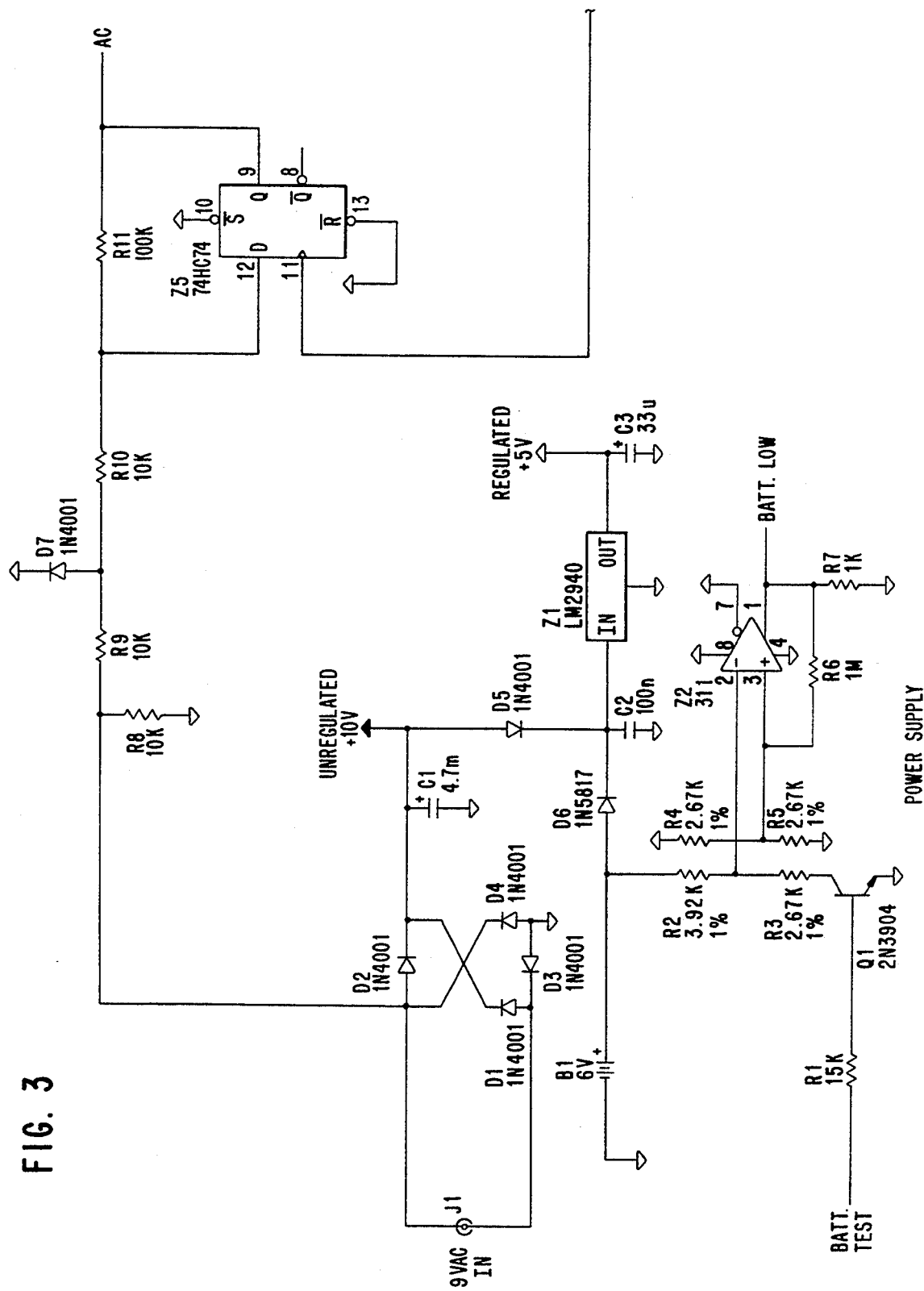
FIGS. 3–5 are more detailed schematics therefor.
Figure 3:
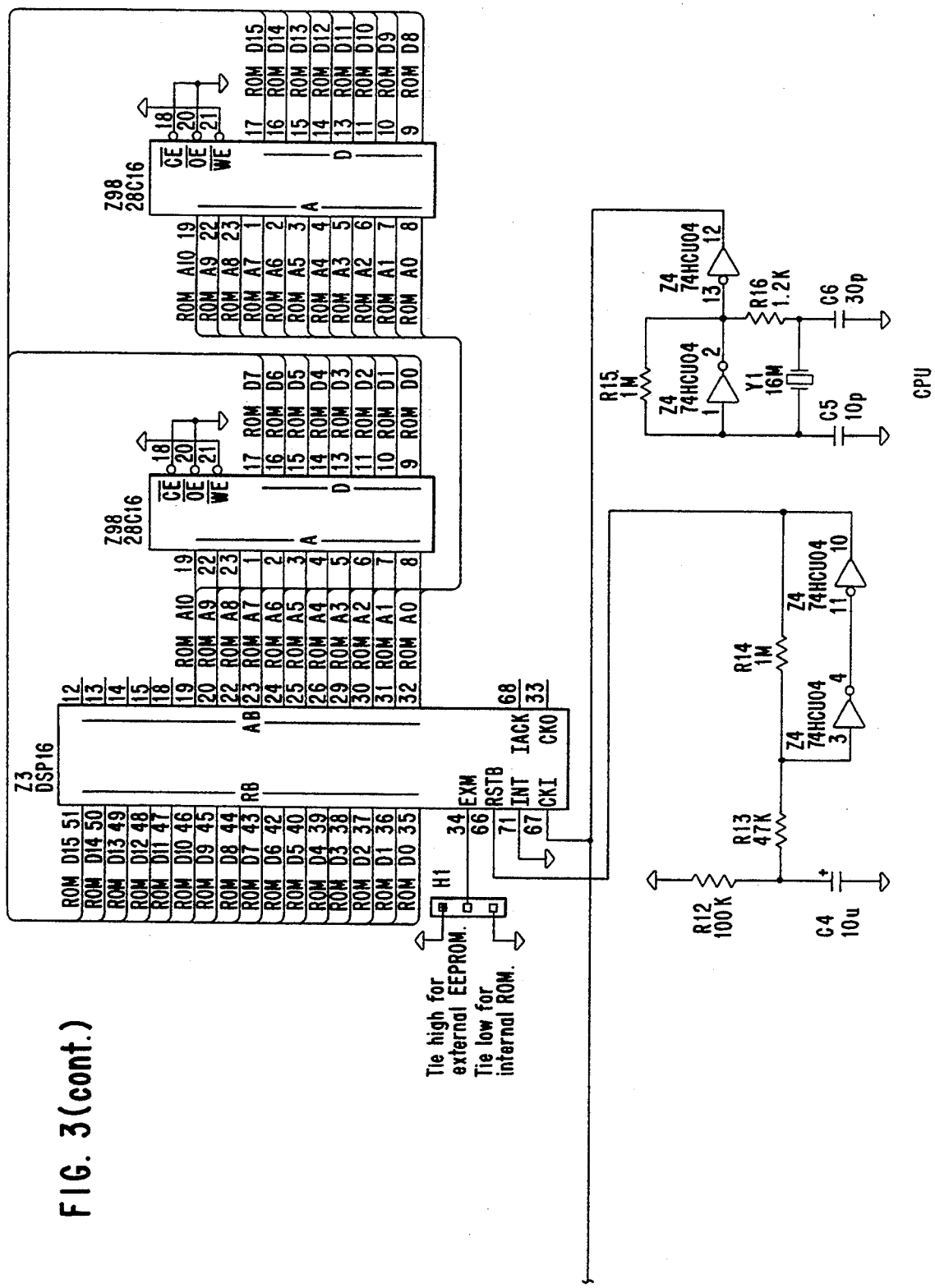
Figure 4:
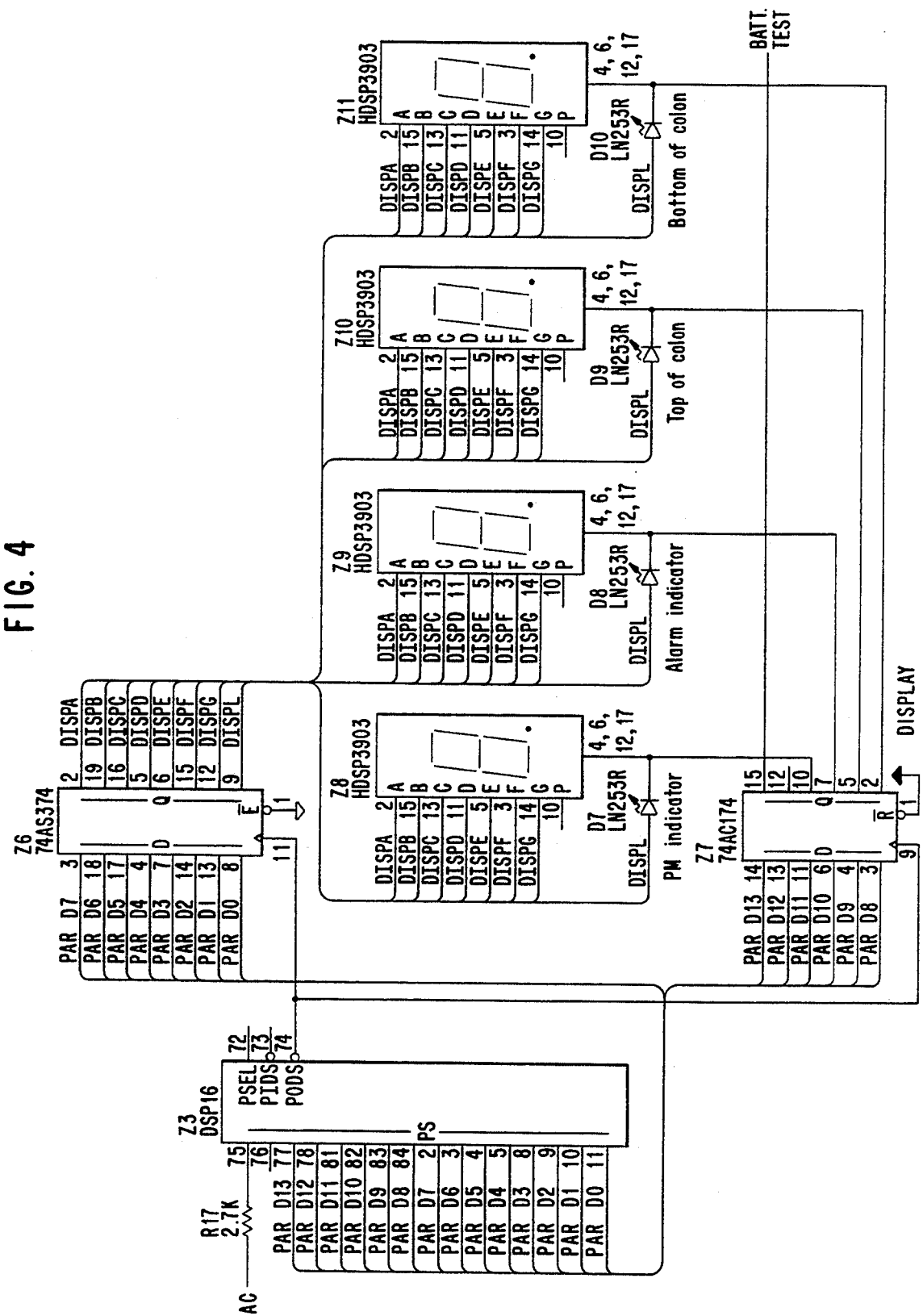
Figure 5:
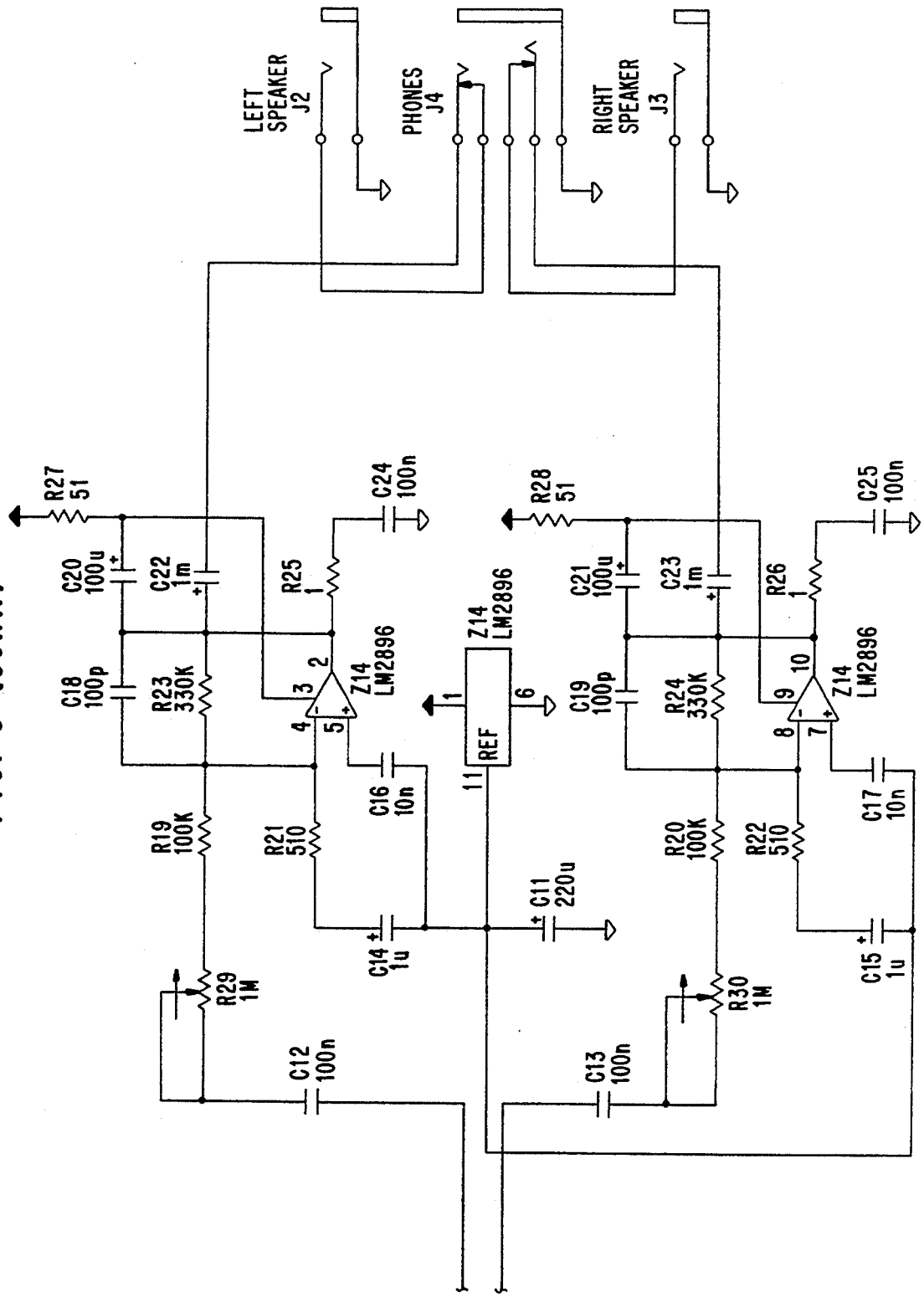

One area of applicability of the techniques of the present invention is in the area of sleep therapy. Many individuals suffer from sleep disorders to varying degrees. It is possible to provide a suitable entrainment environment, based on known sleep cycles prevalent in humans, to help individuals to regulate their sleep patterns, and thus help to solve their sleep disorders. One embodiment of the invention, shown in FIG. 2 and also in FIGS. 3–5, implements the inventive techniques in what the inventor calls a Sleep Processor to aid in the regulation of human sleep cycles.

Figure 1A:
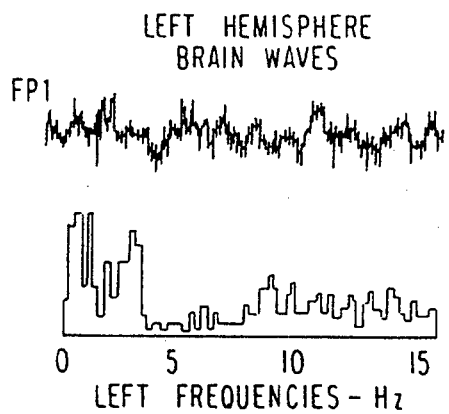
FIGS. 1A–1C and 1D–1F taken from the above-mentioned copending application, show one example of the results which can be achieved using the inventive techniques.
Figure 1B:
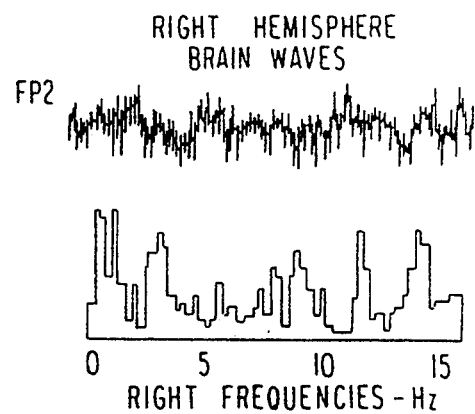
Figure 1C:
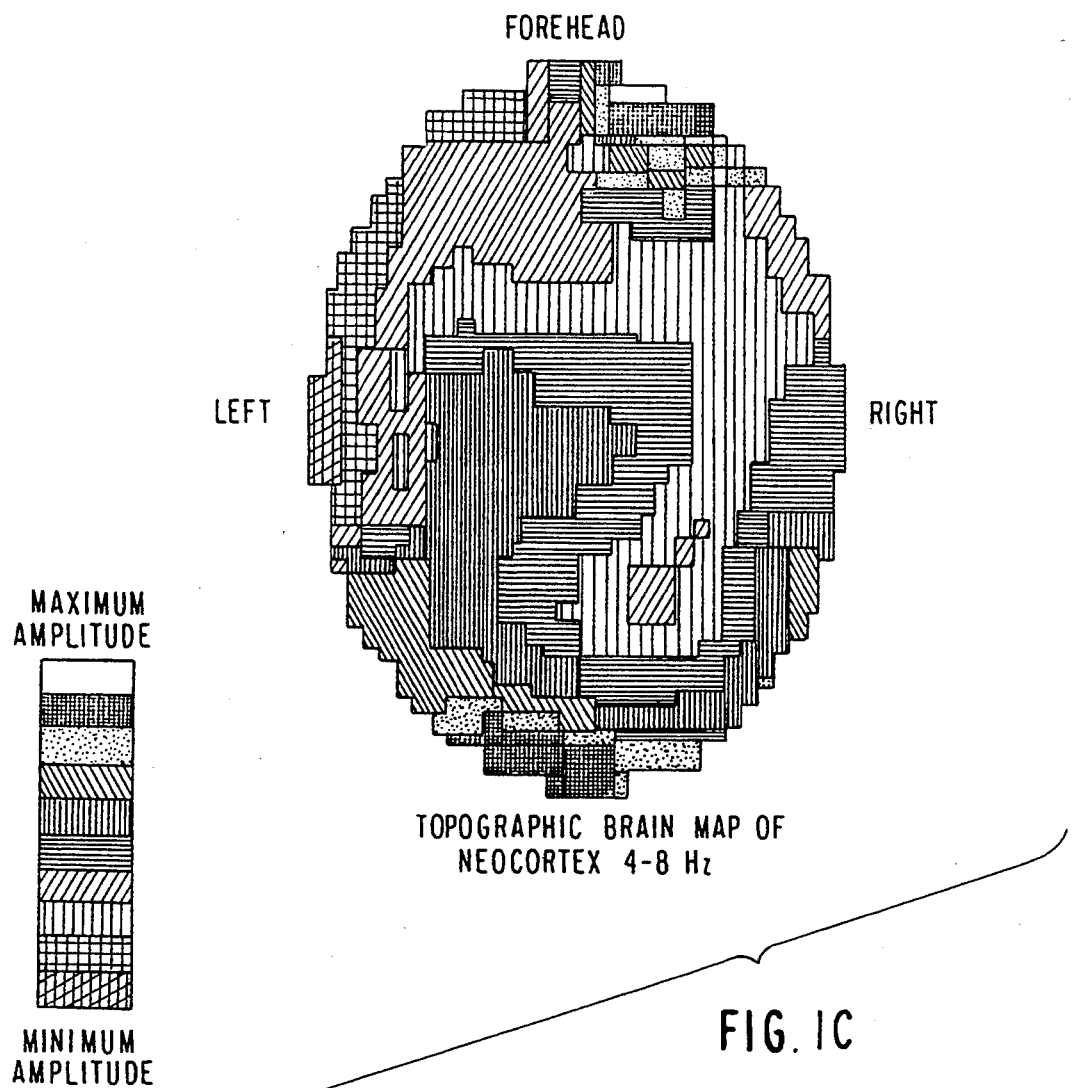
Figure 1D:
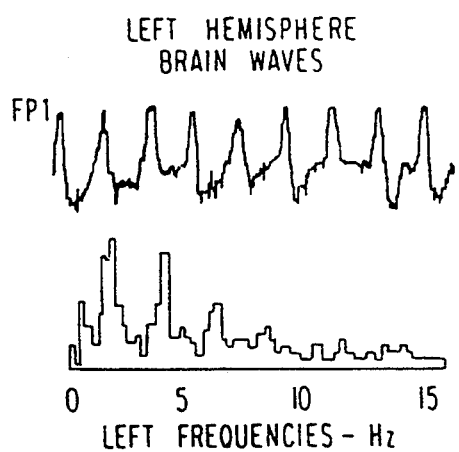
Figure 1E:
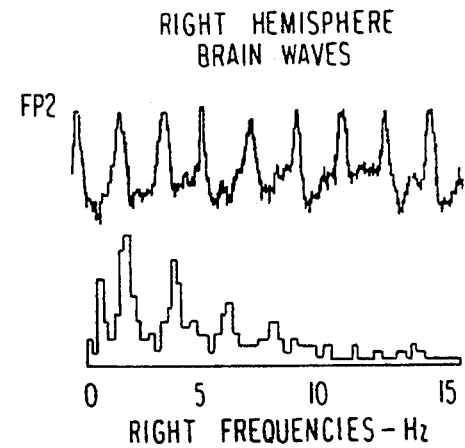
Figure 1F:
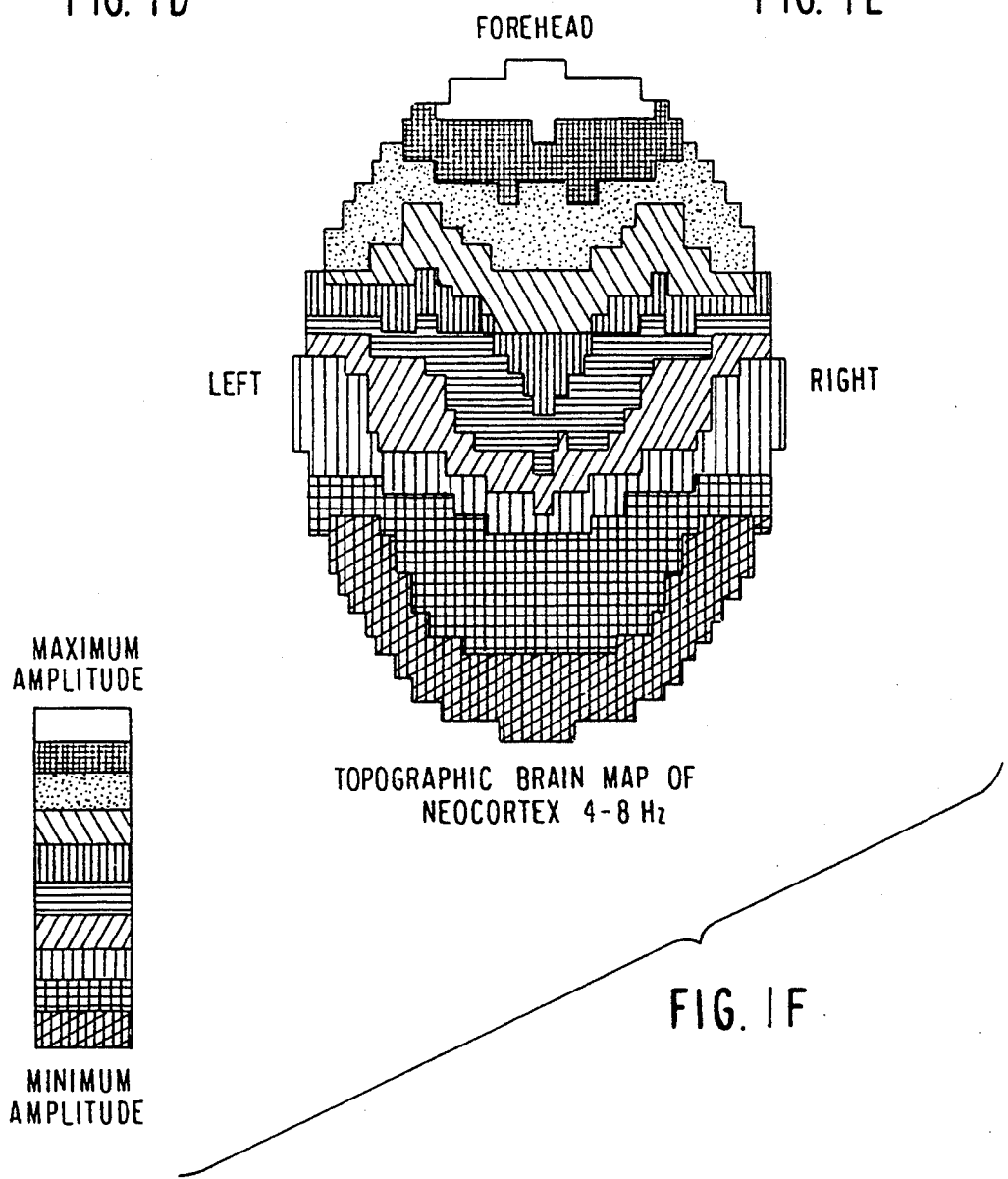
Figure 2:
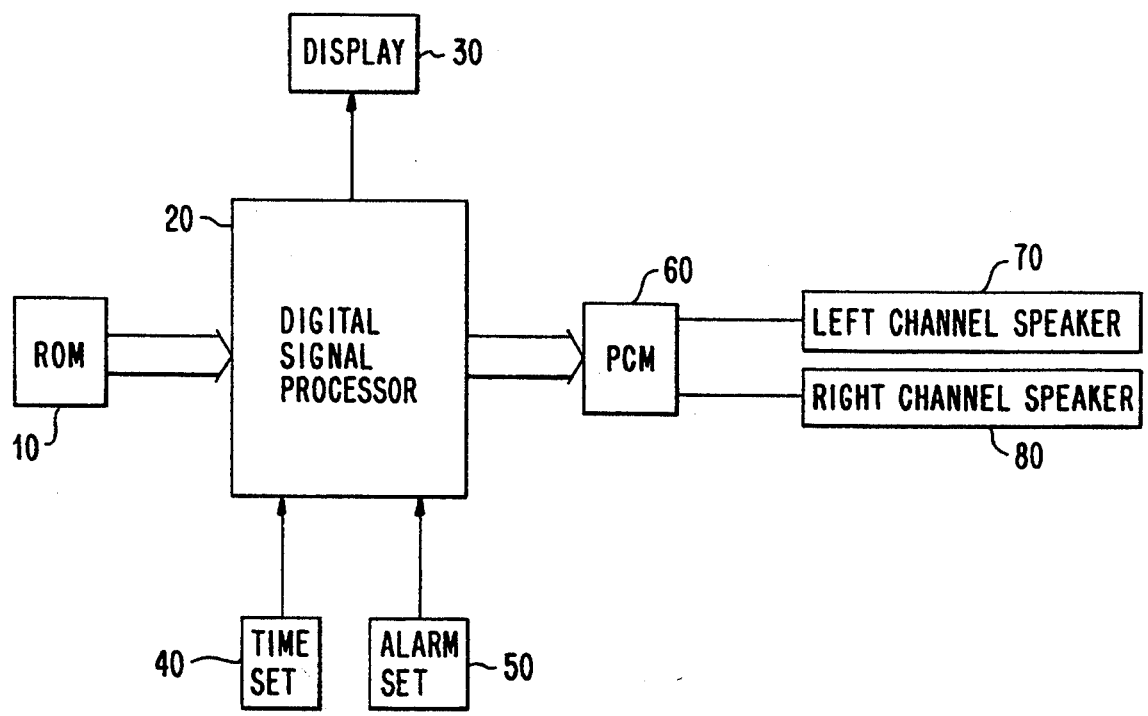
FIG. 2 is a block diagram of the hardware according to a second embodiment of the invention.

In FIG. 2, a read-only memory (ROM) 10 stores frequency sequences corresponding to different parts of a human sleep cycle. The stored frequency sequences may be in accordance with a predetermined algorithm, or alternatively may provide a less complex entrainment environment, such as simple averaging. A digital signal processor (DSP) 20 selects different ones of these sequences based on the current time and the time to which an alarm is set. The time is displayed on display 30, and is set using time set 40. The alarm is set to a desired wake-up time using alarm set 50.

During operation, the DSP 20 accesses the ROM 10 and provides an output to a pulse code modulator unit (PCM) 60 accordingly. The PCM 60 provides an output to each of left and right channel speakers 70, 80 which are provided in close proximity to the ears of a human subject. Using headphones enhances the effect.

Some additional detail of operation of the DSP 20 in one aspect of this embodiment now will be provided. A serial port in the DSP 20 generates an interrupt at a 50 KHz rate. An interrupt handler in the DSP 20 computes the various sounds, in one form, by generating sine waves using a pair of integrators:

cosine = cosine + frequency × sine
sine = sine − frequency × cosine

The Sleep Processors needs ten frequencies, five for each channel, and all of these frequencies are generated at the same time. The results are multiplied by ten envelopes, most of which are zero at any moment.

Noise is generated by a well-known 16-bit shift-register algorithm. This algorithm generates a noise signal that repeats every 65535 samples, or about every five seconds. The noise is filtered to sound more like pink or red noise, and less like white noise, and is written into a delay line in RAM. For each channel, the filtered noise is averaged with an earlier sample from the delay line, thus imparting a comb filter response to it.

An additional low-frequency sine/cosine pair is generated, to sweep the comb filter delay. 32-bit arithmetic is used here. The approximate sweep rate is about 1/8 Hz. The low-frequency sine wave is used directly to sweep the delay on one channel. The delay on the other channel is controlled by some mix of the sine and cosine waves. By choosing these and other coefficients properly, any phase and amplitude relationship between the left and right sweep can be obtained. The comb filtered noise for each channel is multiplied by a noise envelope value.

The device is operated as follows. A desired wake-up time is set, much like an alarm clock, and the desired volume is selected. A start/stop button then is pressed to start the cycles for the selected sleep period. Throughout the sleep period, the device repeats a 90 minute cycle of sound that leads the subject through alpha, theta, delta, and back to dreaming sleep. Five minutes before the scheduled wake-up time, a beta signal is introduced to bring the subject back to complete physical wakefulness. When the subject wakes up, he/-she hits the start/stop button again to stop the sound sequence.

The sounds produced by the DSP 20 include binaural beat carrier sound patterns utilizing both amplitude and frequency modulation, masking pink sound (a known type of sound described in the copending application), and, optionally, occasional single-word voiced affirmations. The binaural beat audio signals may be in the form of appropriate sine waves, or alternatively may be replicas of actual EEG brain waveforms. In the latter case, either the just-described combined EEG waveforms or a single EEG waveform (as described in the copending application) may be used. The entire pattern of sound and control is generated algorithmically.

One aspect of the effectiveness of the device of FIGS. 2-5 is the spacing of sound carriers at related frequencies so as to engender binaural beat signals not only from channel to channel, but also monaurally, in each audio channel. In this preferred embodiment, three binaural beat frequency signals are created between audio carrier channels, and two amplitude beats per channel also are created, yielding a total of seven beat signals. The inventor has coined the term Septon for this set of beat signals. One example of a septon is as follows:

| Left Channel | | Right Channel |
|---|---|---|
| 200 Hz carrier | (4 Hz binaural beat) | 204 Hz carrier |
| (4 Hz monaural beat) | | (4 Hz monaural beat) |
| 204 Hz carrier | (4 Hz binaural beat) | 208 Hz carrier |
| (4 Hz monaural beat) | | (4 Hz monaural beat) |
| 208 Hz carrier | (4 Hz binaural beat) | 212 Hz carrier |

A standard program according to this preferred embodiment would employ the following sound sequence:
0-5 minutes:
Signal Group A (comprised of replicated EEG waveforms having dominant values in the alpha range)
Signal Group B (15 dB below Group A, generated simultaneously with the sounds of Group A, and comprised of replicated EEG waveforms having dominant values in the theta range)
Phased Pink Sound (six seconds, peak-to-peak, on both left and right channels, 20 dB below Group A)
Voice Inserts (repeated at 40 second intervals, 10 dB below Group A, simultaneously with the other sounds, and comprising short sequences of phrases like "relax" "let go", and "sleep")
5-20 minutes:
Signal Group B
Signal Group C (20 dB below Group B, generated simultaneously with Group B, and comprised of replicated EEG waveforms having dominant values in the delta range)
Phased Pink Sound (15 dB below Group B, having a duration as in the first interval)
Voice Inserts (10 dB below Group B, comprised as above)
20-40 minutes:
Signal Group C
Signal Group D (10 dB below Group C, generated simultaneously with Group C, and comprised of replicated EEG waveforms having dominant values in the lower delta range)
Phased Pink Sound (10 dB below Group C, having a duration as in the first interval)
Voice Inserts (20 dB below Group C, comprised as above) 40-65 minutes:
Signal Group D
Phased Pink Sound (10 dB below Group D, having a duration as in the first interval)
Voice Inserts (20 dB below Group D, comprised as above) 65-80 minutes:
Signal Group C
Signal Group D (10 dB below Group C, generated simultaneously with Group C)
Phased Pink Sound (15 dB below Group C, having a duration as in the first interval)

NO voice inserts
80–90 minutes:
Signal Group B
Signal Group C (10 dB below B, generated simultaneously with Group B)
Phased Pink Sound (15 dB below Group B, having a duration as in the first interval)
NO voice inserts The foregoing sequence is repeated through the sleep period until the wakeup sequence, approximately five minutes before the set wake-up time:
Signal Group AA (a wakeup sequence, comprising replicated EEG waveforms having dominant values in the beta range, or alternatively a 400 Hz/416 Hz envelope yielding frequencies in the beta range)
Voice inserts (10 dB below Group AA, comprised of short phrases such as "waking up", "refreshed", "bright", and repeated at intervals)

One variation of the foregoing embodiment is an alarm clock which, instead of sounding a loud alarm or other jarring noise at wake-up time, starts a gentle sequence of signals some minutes before, to bring an individual up gently through the various levels of sleep to full wakefulness. A fade-in theta-alpha signal may be provided, followed by a stronger beta-gamma signal.

FIGS. 6A to 6J show the effects of the just-described "sleep processor" embodiment. Column 1 shows distribution of delta frequencies; column 2 shows distribution of theta frequencies; and column 3 shows distribution of alpha frequencies. The top row of graphs is the actual pattern observed in the individual, and the bottom row is the baseline pattern.

Figure 6A:
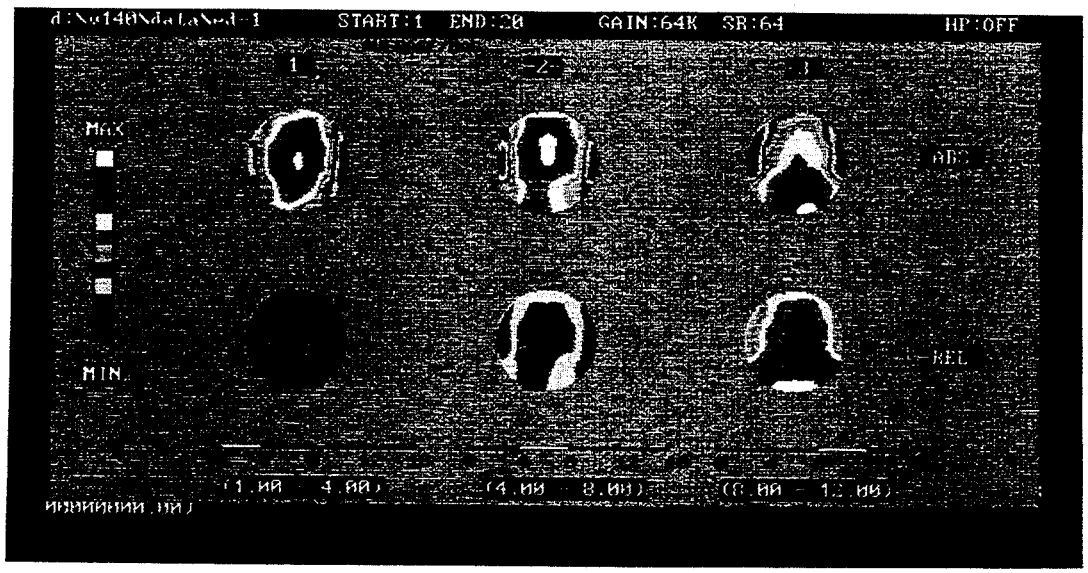
FIGS. 6A–6J are drawings, similar to FIGS. 1A and 1B, but showing brain activity during various stages of a sleep cycle, using a technique in accordance with the second embodiment of the invention.
Figure 6B:
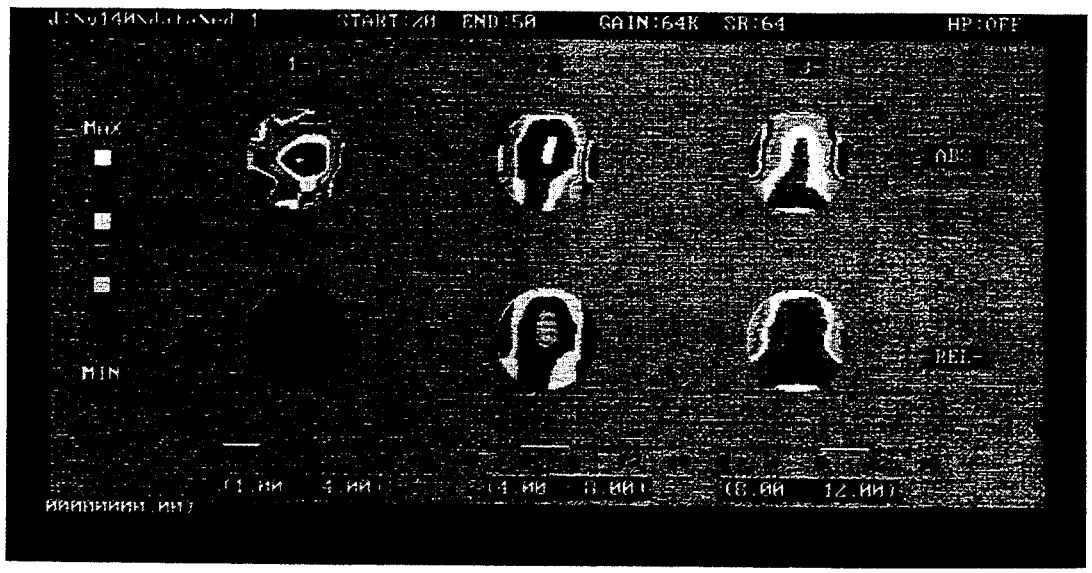

FIG. 6A corresponds to a normal waking state. Dominant alpha activity is shown in the occipital area of the brain. In FIG. 6B, pink noise has been applied, without any beat frequencies. A narrower focus of waking state is shown.

Figure 6C:
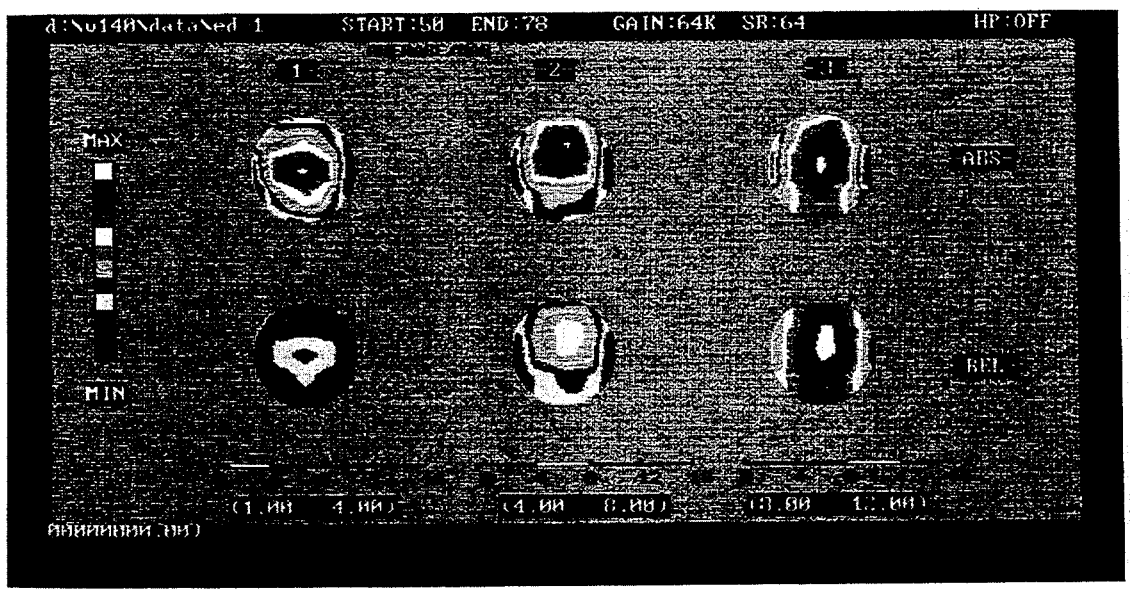
Figure 6D:
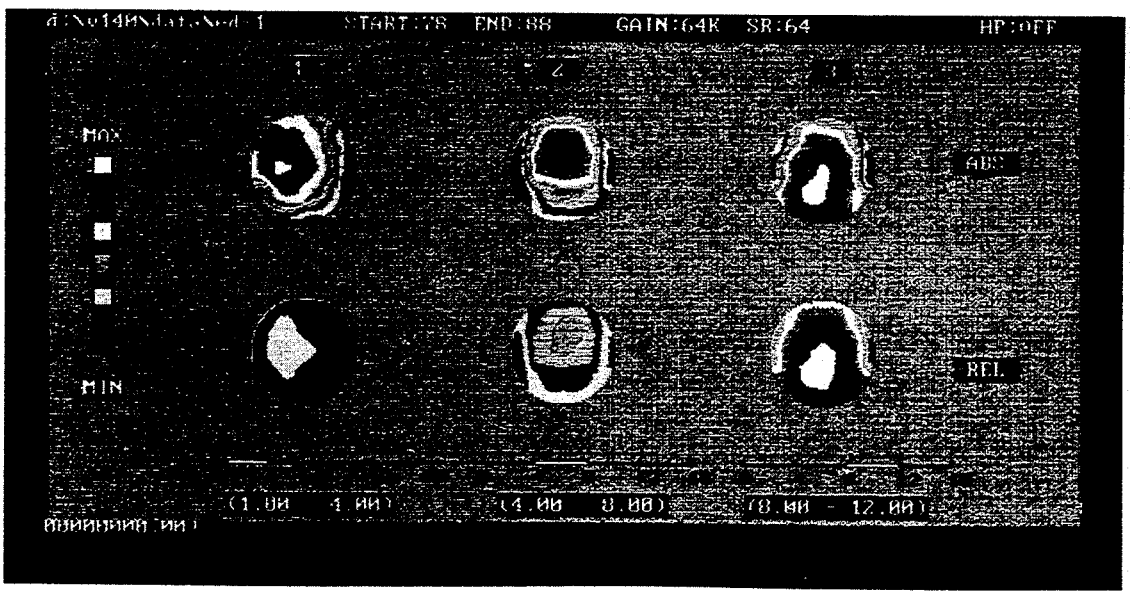

In FIG. 6C, a signal sequence corresponding to Signal Group A has been applied. Some gain in theta frequencies are seen, with rapid diffusion of alpha frequencies and movement toward the vertex of the head. In FIG. 6D, a signal sequence corresponding to Signal Group B has been applied. There is further diffusion of alpha frequencies, with some movement of delta and theta activity toward the pre-frontal cortex of the brain.

Figure 6E:
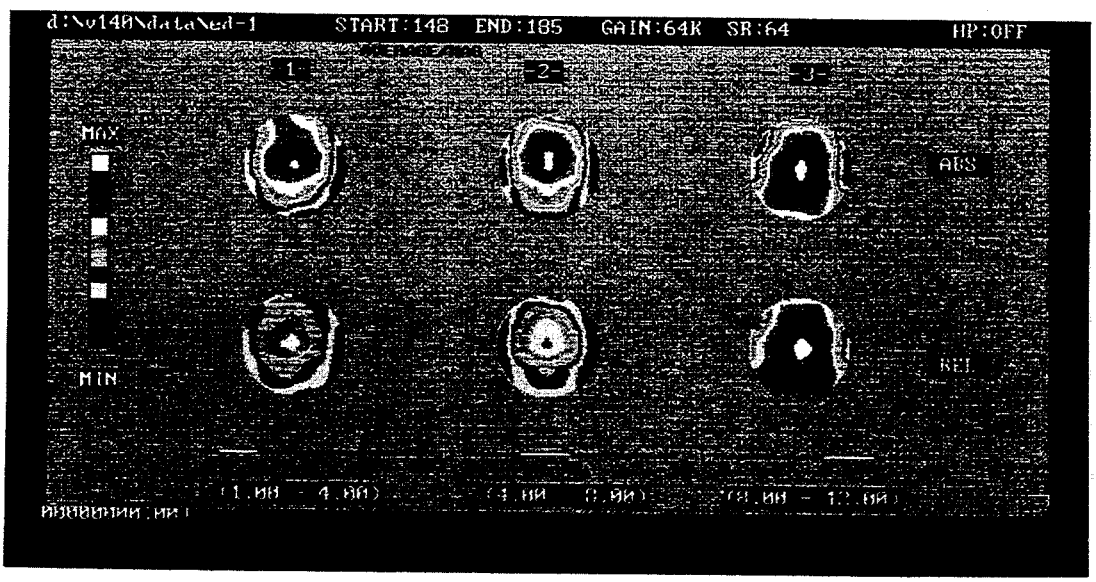
Figure 6F:
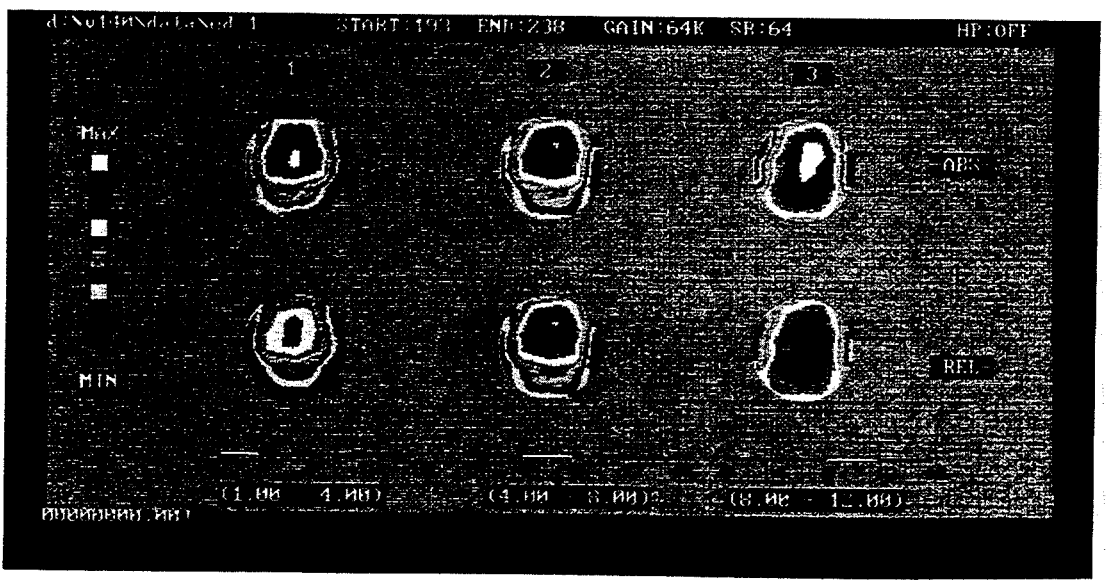

In FIG. 6E, a signal sequence corresponding to Signal Group C has been applied. There is rapid diffusion of alpha frequencies, and increased power of theta and delta frequencies. In FIG. 6F, a signal sequence corresponding to Signal Group D has been applied. Alpha frequencies are diffused further toward the pre-frontal cortex, and there is a marked increase in theta and delta frequencies.

Figure 6G:
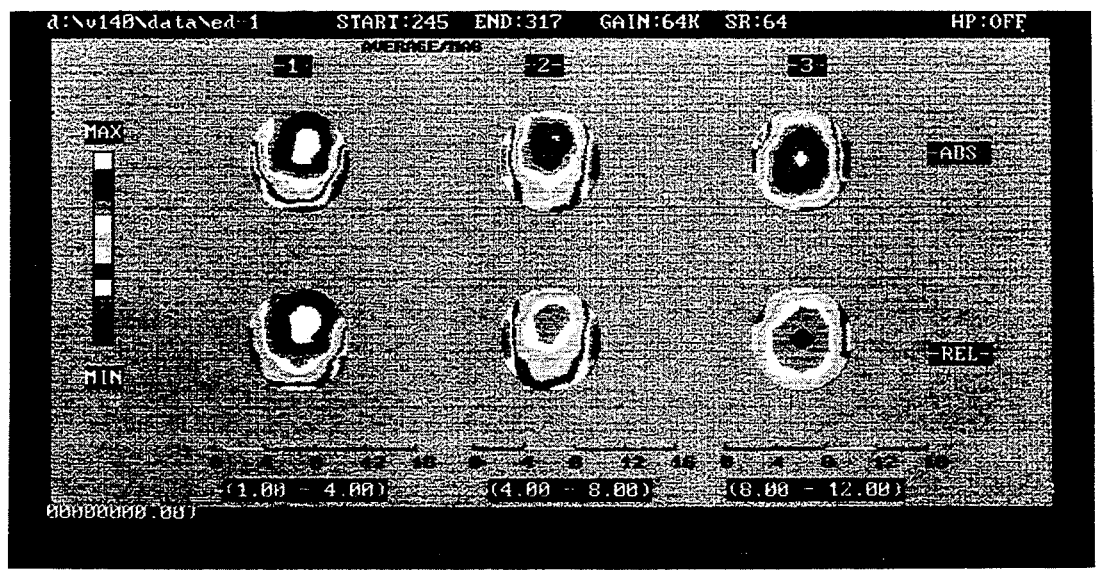
Figure 6H:
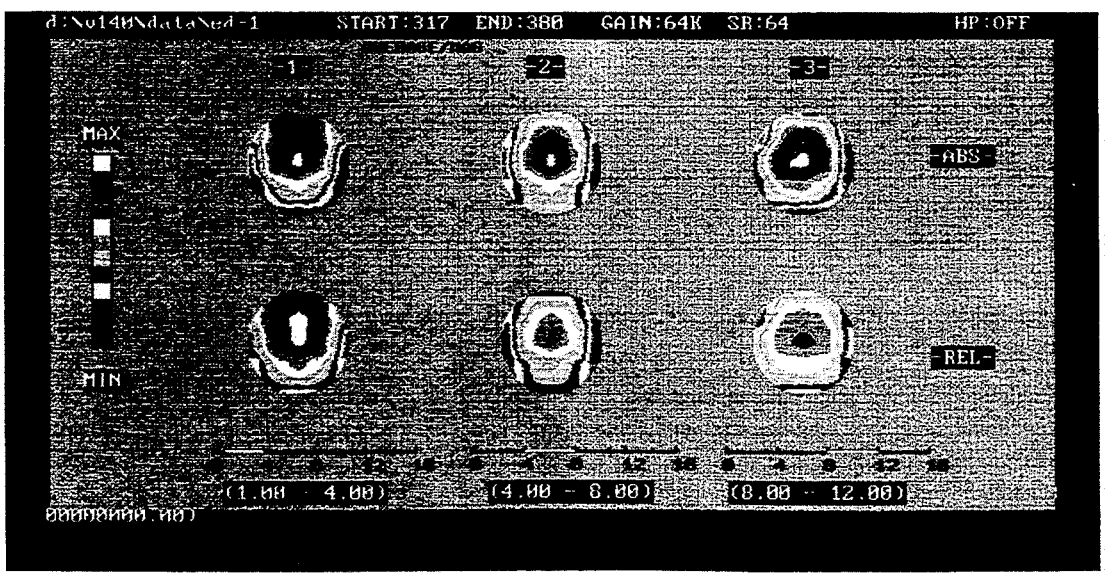
Figure 6I:
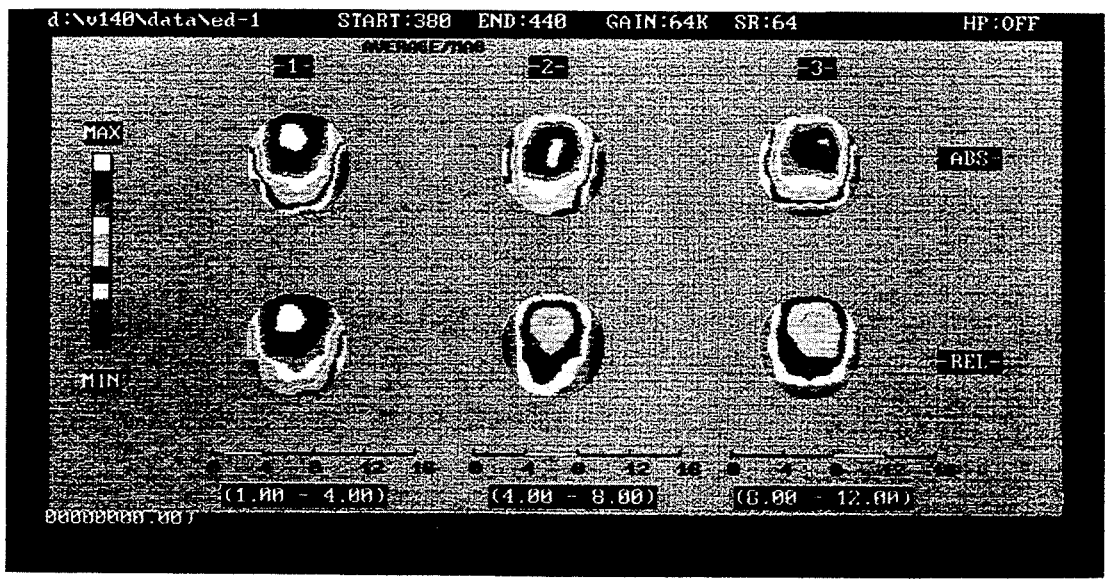
Figure 6J:
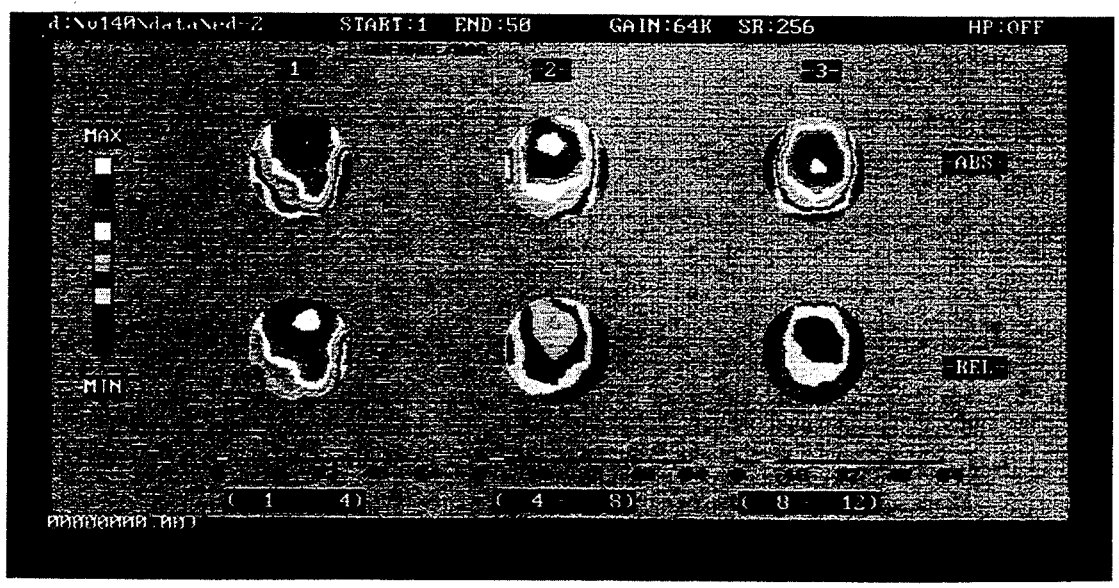

FIG. 6G, continuing application of Signal Group D frequencies, shows a marked increase in delta activity in the pre-frontal cortex, with a steady decrease in alpha activity at the vertex. In FIG. 6H, another binaural beat stimulation has been applied, and characteristics of stage 3 and 4 sleep may be observed. In FIG. 6I, further evidence of the further binaural beat stimulation is observed. Delta is the dominant frequency here. Alpha and theta activity has moved to the prefrontal cortex. Finally, FIG. 6J shows early awakening activity, with a diffusion of delta activity.

Figure 7:
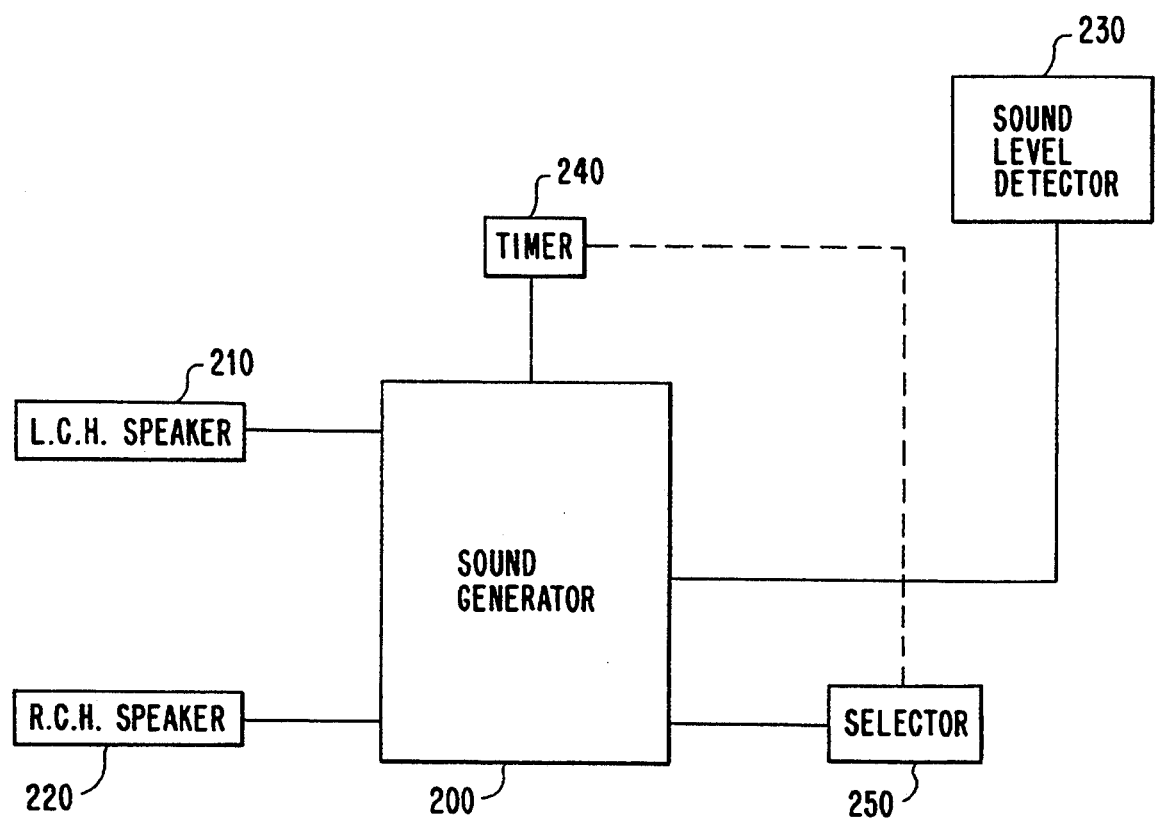
FIG. 7 is a block diagram of hardware in accordance with a third embodiment of the invention.

FIG. 7 is a block diagram of hardware in accordance with another embodiment of the invention, having application to the work environment, or anywhere a constant source of noise is present, to allow workers, for example, to maintain a desired state of awareness. The device may contain suitable digital signal processor circuitry, as in the preceding embodiment. One difference is that the operation of the device is keyed to the presence of ambient noise, not to a given time duration or selected sleep period.

The device of FIG. 7 includes a sound generator 200 which, as just mentioned, may comprise a digital signal processor. The generator 200 outputs sound patterns via one or more speakers (left and right channel speakers 210, 220 are shown). A sound level detector 230 detects the level of ambient noise in the room, and provides a signal to the sound generator 200, or activates a cut-off switch (not shown), to discontinue output of the sound generator 200 when the ambient noise level drops below a predetermined level.

The sound level detector also preferably provides a signal to the sound generator 200 to boost the sound pattern output when the ambient noise level increases, so that the effect of the provision of the sound pattern is commensurate with the noise level in the room. Alternatively, the user may simply adjust the volume manually, using one or more knobs (not shown) on the sound generator 200.

A timer 240 may be provided to control the duration of provision of the selected sound pattern, or even to change the sound pattern at different times of day by controlling a selector 250 which the user accesses to select a particular sound pattern to be output. The user may select a given sound pattern in the morning, and the timer 240 may change that pattern automatically, based on a need at different times of day for sound patterns providing different states of alertness.

The sound pattern produced by the device of FIG. 7 varies automatically in amplitude in accordance with changes in the ambient noise, and is discontinued when the noise stops. As a result, the sound remains unobtrusive. Depending on the setting, the produced sound pattern can enhance wakefulness, promote relaxation (as, for example, in rest areas in the workplace), reduce anxiety and stress, or focus attention, among other characteristics.

The basic system of FIG. 7 produces and inserts four different sound patterns which are selected manually so as to merge the output into the constant ambient noise. More sound patterns are possible, depending on the desired overall capabilities of the system. Various modifications are possible. For example, a programmable version may be provided, which changes the form of the sound patterns throughout a work day or night, in accordance with the responses desired.

Selectability of patterns may be accomplished differently in a model intended for use in conjunction with a computer system. The computer operator can input a selection, and may vary that selection as desired throughout the work day.

Figure 8A:
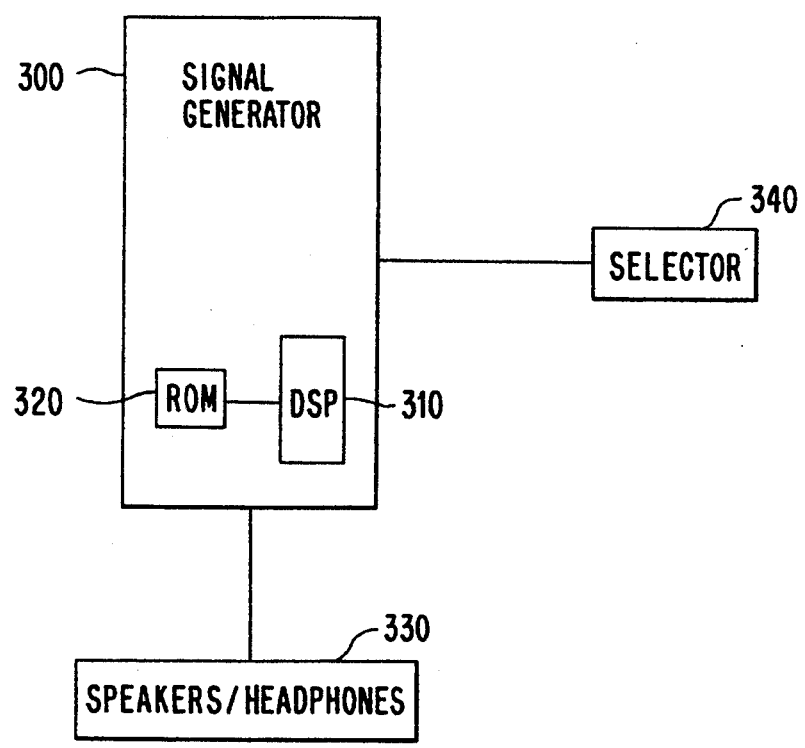
FIG. 8A is a block diagram of hardware in accordance with a fourth embodiment of the invention, and FIG. 8B a schematic of that hardware.

FIG. 8A is a diagram of a portable embodiment of the invention, for use in providing a desired level of consciousness on an individualized basis. A signal generator 300 preferably includes a digital signal processor 310 and a ROM 320 for storing predetermined signals or sequences of signals which correspond to various desired states of awareness. The signal generator 300 may be a simple tone generator or pair of tone generators which provide outputs to speakers or headphones 330 (such as button-sized headphones) to set up a binaural beat. Output of pink sound or phased pink sound by the generator 300 is desirable to facilitate defocusing of the listener and consequent ability to concentrate on the sounds being produced. A selector 340 enables a user to instruct the signal generator 300 to output signals corresponding to the level of consciousness (e.g. focused concentration, relaxation, alertness) that a user desires.

Figure 8B:
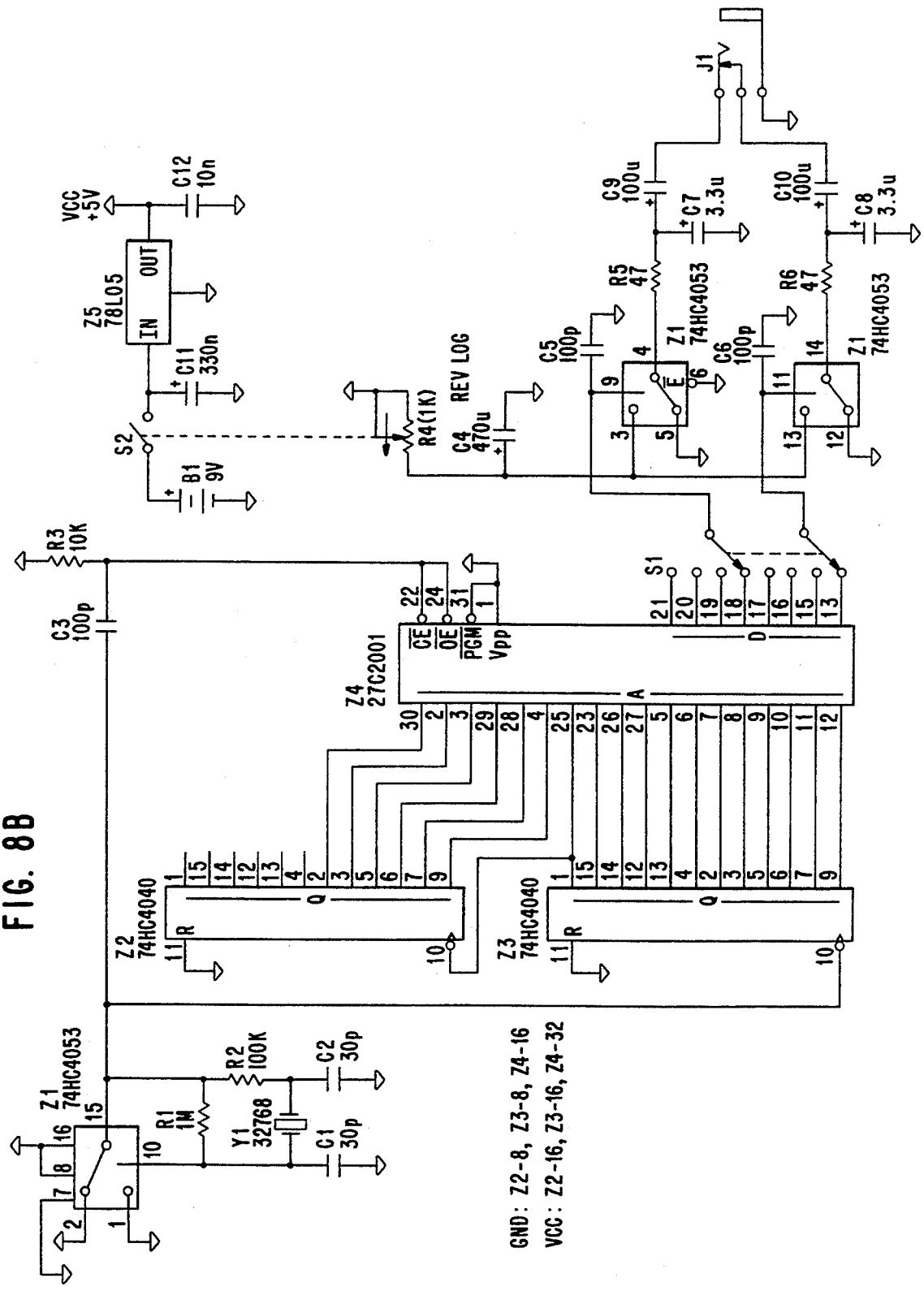

FIG. 8B shows a schematic of this embodiment, which the inventor calls a "Mood Minder". This embodiment includes a selector for selecting one of four possible types of signals, corresponding to four respective levels of awareness: awake and alert; concentration; attention; and relaxation. However, the invention is not so limited, as the generator 300 may be capable of producing other possible types of signals. Alternatively, pre-set patterns in the generator 300 may vary when specialized use is required. The key to this embodiment is its portability, enabling the user to carry the device everywhere. The device is battery-operated, and is small enough to fit in an upper coat pocket, for example.

Figure 9A:
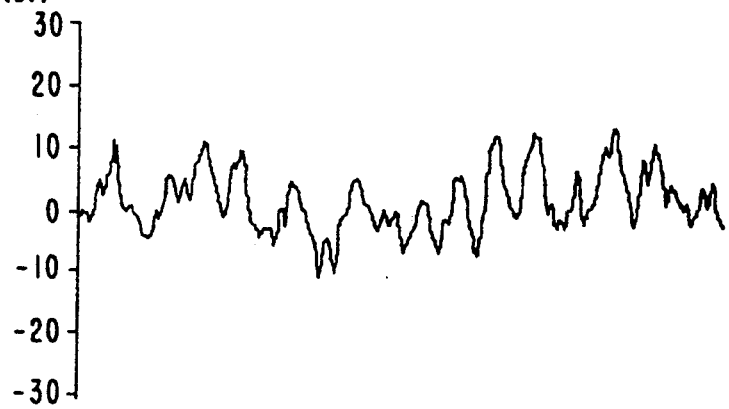
Figure 9E:
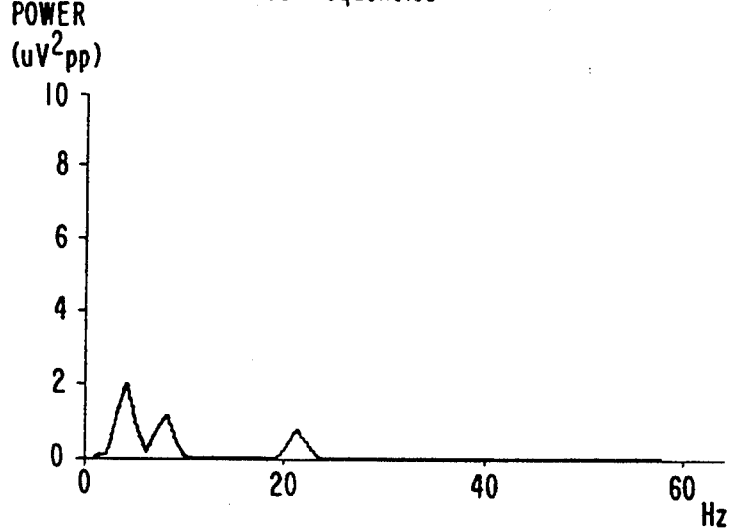
Figure 9F:
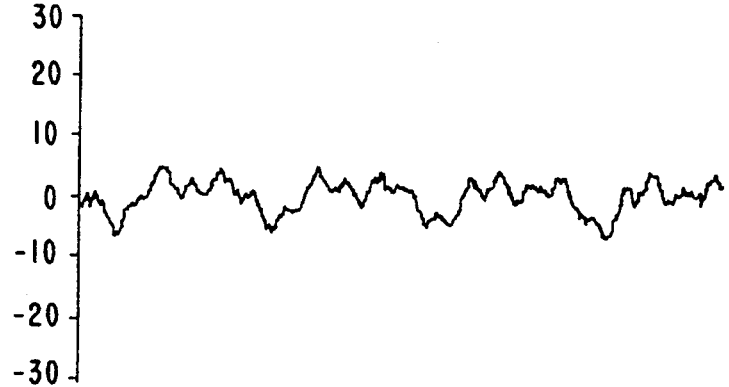
Figure 9G:
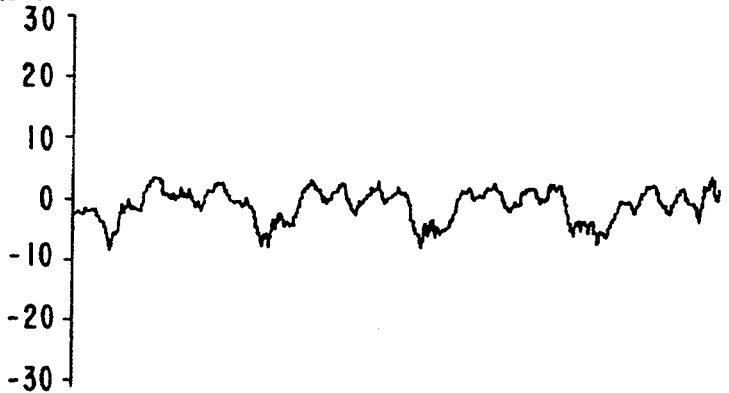
Figure 9H:
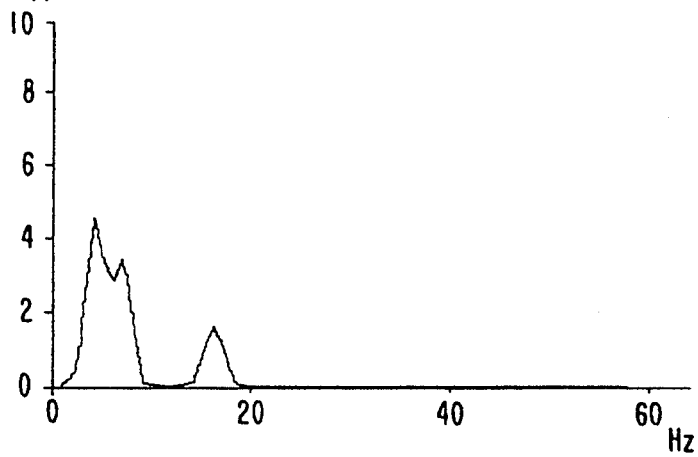
Figure 9I:
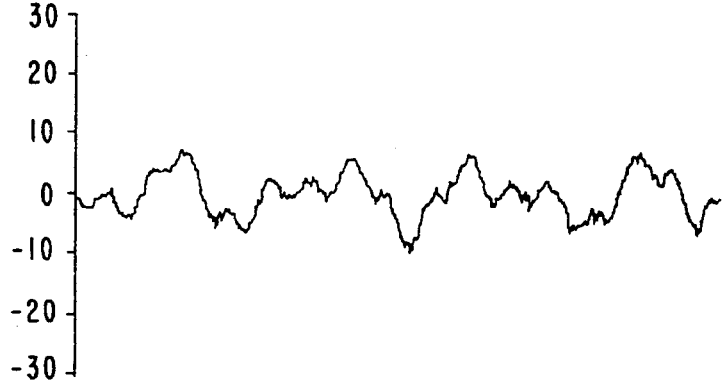
Figure 9J:
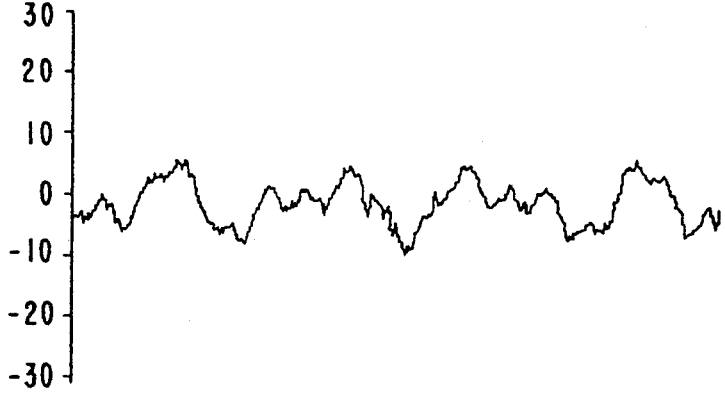
Figure 9K:
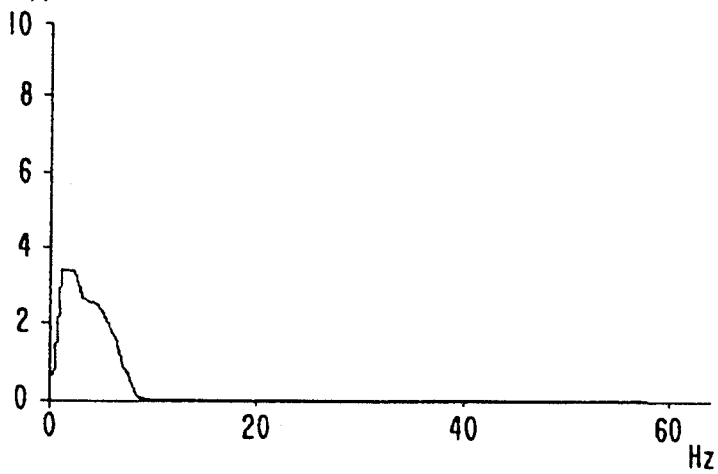
Figure 9L:
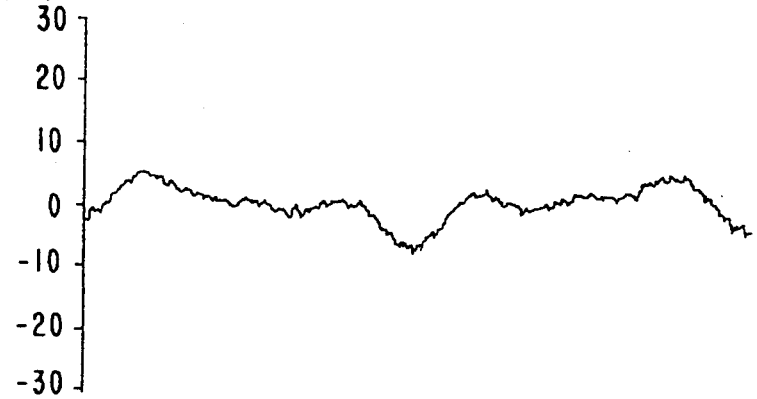
Figure 9M:
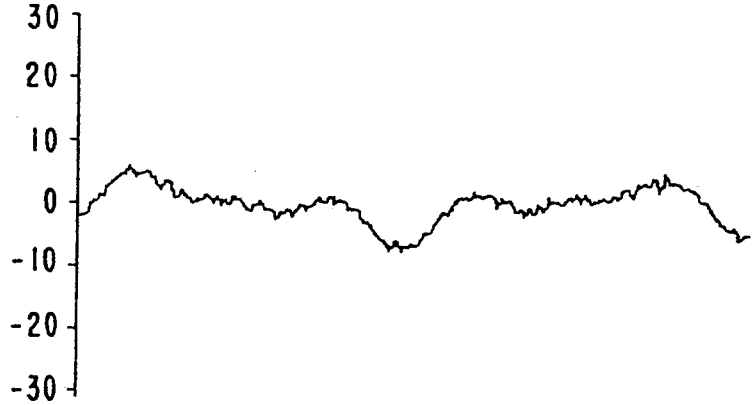

FIGS. 9A-9M show examples of prestored patterns produced by the generator 300, and of results achieved in use. FIG. 9A shows baseline brain waves, with relative power output shown at the right for different frequencies. FIGS. 9B, 9E, 9H, and 9K show the stimulus frequencies produced for four different respective states of consciousness. FIGS. 9C, 9F, 9I, and 9L show the stimulus waves corresponding to the superposition of the stimulus frequencies on the baseline wave. FIGS. 9D, 9G, 9J, and 9M show the results achieved in use. As can be seen, the peak-to-peak amplitudes for the response brain waves correspond closely to those of the stimulus waves.

While the present invention has been described in detail with reference to preferred embodiments, various modifications within the scope and spirit of the invention will be apparent to those of working skill in this technological field. Consequently, the invention should be considered as limited only by the scope of the appended claims.

What is claimed is:

1. A method of inducing desired states of consciousness in human beings, comprising the following steps:
   combining a plurality of replicated electroencephalogram (EEG) waveforms, each indicative of a particular desired state of consciousness, to produce a combined EEG waveform;
   superimposing said combined EEG waveform on two separate sets of carrier waves using stereo sound;
   creating differential beat frequencies between said sets of carrier waves based on said superimposing step; and
   providing the resulting signals in audio form to respective ears of a human being, to induce said state of consciousness.

2. A method as claimed in claim 1, wherein said combining step comprises mathematically averaging said EEG waveforms to produce said combined EEG waveform.

3. A method as claimed in claim 1, further comprising the step of repeating said combining, superimposing, and creating steps for each of a set of desired states of consciousness, and producing a cycle of sets of resulting audio signals, said providing step comprising providing said cycle of sets of resulting audio signals to respective ears of a human being, to induce each of said desired states of consciousness in cyclic fashion.

4. A method as claimed in claim 3, wherein said cycle corresponds to human sleep patterns, said desired states of consciousness comprising wakefulness, alpha sleep, delta sleep, and theta sleep.

5. A method as claimed in claim 3, wherein said cycle corresponds to human sleep patterns, said desired states of consciousness comprising alpha sleep, delta sleep, and theta sleep, said cycle being approximately 90 minutes long.

6. A method as claimed in claim 5, said method further comprising the steps of providing a plurality of repetitions of said cycle, followed by providing a set of audio signals containing a binaural beat at a frequency indicative of beta consciousness.

7. A method as claimed in claim 1, wherein said creating step includes the step of combining pink sound with said sets of carder waves by shifting of said pink sound with respect to said combined EEG waveform from one stereo audio channel to another, with cyclic changes in amplitude, frequency, and rate of panning.

8. Apparatus for facilitating sleep in a human subject, comprising:
   means for setting a wake-up time to select a desired sleep duration;
   means for generating a first sequence of signals in a cycle corresponding to a human sleep pattern, frequencies of said signals in said first sequence being substantially equal to frequencies of human brain patterns at different levels of sleep;
   means for repeating said cycle a plurality of times based on the selected wake-up time; and
   means for waking up said human subject at the selected wake-up time.

9. Apparatus as claimed in claim 8, wherein said means for waking up said human subject comprises means for generating a second sequence of signals a predetermined time before the selected wake-up time, frequencies of said signals in said second sequence being substantially equal to frequencies of human brain patterns at or near an awakened state.

10. Apparatus as claimed in claim 9, wherein said predetermined time is approximately five minutes.

11. Apparatus as claimed in claim 8, wherein said first sequence of frequencies comprises, in order, alpha frequencies, theta frequencies, delta frequencies, and theta frequencies.

12. Apparatus as claimed in claim 8, further comprising means for generating phased pink sound in conjunction with said first sequence of frequencies.

13. Apparatus as claimed in claim 8, wherein said first sequence of signals comprises a plurality of sets of combined brainwaves, each of said sets corresponding to a different level of sleep, said combined brainwaves within a given set being constituted by combined electroencephalogram (EEG) waveforms of a plurality of individuals, taken when said individuals had attained a different respective level of sleep.

14. Apparatus as claimed in claim 13, wherein said EEG waveforms are mathematically averaged.

15. Apparatus for awakening an individual using brain pattern entrainment, said apparatus comprising:
   means for selecting a wake-up time;
   means for keeping time; and
   means, operative a predetermined period before said wake-up time as determined by said means for keeping time, for producing a first sequence of signals having frequencies in the theta-alpha range, followed by a second sequence of signals having frequencies in the beta-gamma range.

16. Apparatus as claimed in claim 15, wherein said means for producing said first and second sequences of signals comprises means for producing said second sequence of signals at a higher amplitude than said first sequence of signals.

17. Apparatus as claimed in claim 15, wherein said first sequence of signals comprises a plurality of sets of combined brainwaves, each of said sets corresponding to a different level of consciousness, said combined brainwaves within a given set being constituted by combined electroencephalogram (EEG) waveforms of a plurality of individuals, taken when said individuals had attained a different respective level of consciousness.

18. Apparatus as claimed in claim 16, wherein said EEG waveforms are mathematically averaged.

19. Apparatus for inducing a desired state of consciousness, said apparatus comprising:
   means for detecting presence of a predetermined level of ambient noise;
   means, responsive to said detecting means, for generating signals having frequencies substantially equal to frequencies of human brain patterns when said ambient noise is present; and
   means for selecting said signals in accordance with desired human activity in said areas.

20. Apparatus as claimed in claim 19, further comprising timer means, connected to said generating means, for generating said signals for a predetermined time set by said timer means.

21. Apparatus as claimed in claim 19, wherein said timer means is connected to said selecting means to enable selection of different ones of said signals in accordance with desired human activity at different times of day.

22. Apparatus as claimed in claim 19, wherein said generating means comprises means, responsive to said detecting means, for increasing an amplitude of said signals in response to an increase in amplitude of said ambient noise, and for decreasing an amplitude of said signals in response to a decrease in amplitude of said ambient noise.

23. Apparatus as claimed in claim 22, wherein said generating means further comprises means for discontinuing said signals when said ambient noise falls below said predetermined level.

24. Apparatus as claimed in claim 19, wherein said generating means comprises a digital signal processor and a read-only memory (ROM) connected to said digital signal processor, said ROM storing a plurality of sets of signals, each of said sets of signals having frequencies substantially equal to human brain patterns at a desired state of consciousness.

25. Apparatus as claimed in claim 24, wherein each of said sets of signals comprises a plurality of sets of combined brainwaves, each of said sets corresponding to a different level of consciousness, said combined brainwaves within a given set being constituted by combined electroencephalogram (EEG) waveforms of a plurality of individuals, taken when said individuals had attained a different respective state of consciousness.

26. Apparatus as claimed in claim 25, wherein said EEG waveforms are mathematically averaged.

27. Apparatus for awakening an individual using brain pattern entrainment, said apparatus comprising:
   means for selecting a wake-up time; and
   means, operative a predetermined period before said wake-up time, for producing a first sequence of signals having frequencies in a first predetermined range corresponding to a first state of consciousness, followed by a second sequence of signals having frequencies in a second predetermined range corresponding to a second state of consciousness.

28. Apparatus as claimed in claim 27, wherein said first predetermined range is the theta-alpha range, and said second predetermined range is the beta-gamma range.

* * * * *